(12) United States Patent
Sun et al.

(10) Patent No.: US 9,188,556 B2
(45) Date of Patent: Nov. 17, 2015

(54) TEMPERATURE SENSING ANALYTE SENSORS, SYSTEMS, AND METHODS OF MANUFACTURING AND USING SAME

(75) Inventors: Hoi-Cheong Steve Sun, Tampa, FL (US); John P. Creaven, Pearl River, NY (US); Mu Wu, Hopewell Junction, NY (US); Paul M. Ripley, Nanuet, NY (US); Steven C. Charlton, Osceola, IN (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 208 days.

(21) Appl. No.: 13/884,694

(22) PCT Filed: Nov. 7, 2011

(86) PCT No.: PCT/US2011/059569
§ 371 (c)(1),
(2), (4) Date: Jul. 15, 2013

(87) PCT Pub. No.: WO2012/064645
PCT Pub. Date: May 18, 2012

(65) Prior Publication Data
US 2013/0298648 A1    Nov. 14, 2013

Related U.S. Application Data

(60) Provisional application No. 61/413,365, filed on Nov. 12, 2010.

(51) Int. Cl.
*G01N 27/327* (2006.01)
*G01N 25/00* (2006.01)
(Continued)

(52) U.S. Cl.
CPC .............. *G01N 25/00* (2013.01); *A61B 5/1486* (2013.01); *A61B 5/14532* (2013.01);
(Continued)

(58) Field of Classification Search
CPC ............. A61B 5/14532; A61B 5/1486; A61B 2562/12; A61B 2560/0252; A61B 2560/0285; G01N 25/00; G01N 27/3274; Y10T 29/49117
USPC .............. 73/61.41, 61.46, 61.76; 204/403.01; 29/825
See application file for complete search history.

(56) References Cited

U.S. PATENT DOCUMENTS

2008/0249385 A1* 10/2008 Phan ............................ 600/347
2009/0000947 A1* 1/2009 Akahori et al. ........... 204/403.14
(Continued)

FOREIGN PATENT DOCUMENTS

| EP | 0 969 282 | 1/2000 |
|---|---|---|
| JP | 2006-038841 | 2/2006 |

(Continued)

OTHER PUBLICATIONS

International Preliminary Report on Patentability and Written Opinion of International Application No. PCT/US2011/059569 mailed May 23, 2013.
(Continued)

*Primary Examiner* — Daniel S Larkin
(74) *Attorney, Agent, or Firm* — Dugan & Dugan, PC

(57) ABSTRACT

An analyte sensor is provided for detecting an analyte concentration level in a bio-fluid sample. The analyte sensor has a base, a first electrode and a second electrode wherein a thermocouple portion is provided integral with the second electrode thereby enabling on-sensor temperature measurement capability. In some embodiments, two and only two electrical contact engagement portions are provided thereby simplifying electrical contact. Manufacturing methods and systems utilizing the analyte sensors are provided, as are numerous other aspects.

20 Claims, 10 Drawing Sheets

(51) Int. Cl.
*A61B 5/145* (2006.01)
*A61B 5/1486* (2006.01)

(52) U.S. Cl.
CPC .... *G01N 27/3274* (2013.01); *A61B 2560/0252* (2013.01); *A61B 2560/0285* (2013.01); *A61B 2562/12* (2013.01); *Y10T 29/49117* (2015.01)

(56) References Cited

U.S. PATENT DOCUMENTS

| | | | |
|---|---|---|---|
| 2009/0325205 A1* | 12/2009 | Fujii et al. | 435/14 |
| 2010/0288841 A1* | 11/2010 | Ripley et al. | 235/469 |
| 2011/0073476 A1 | 3/2011 | Gofman et al. | |
| 2012/0032774 A1* | 2/2012 | Jung et al. | 337/414 |

FOREIGN PATENT DOCUMENTS

| | | |
|---|---|---|
| JP | 2010-025926 | 2/2010 |
| WO | WO 2010/151592 | 12/2010 |
| WO | WO 2012/064645 | 5/2012 |

OTHER PUBLICATIONS

Invitation to Pay Additional Fees and Partial Search Report of International Application No. PCT/US2011/059569 mailed Mar. 29, 2012.

International Search Report and Written Opinion of International Application No. PCT/US2011/059569 mailed Jun. 11, 2012.

Japanese Office Action of Japanese Application No. 2013-538807 dated Mar. 24, 2015.

* cited by examiner

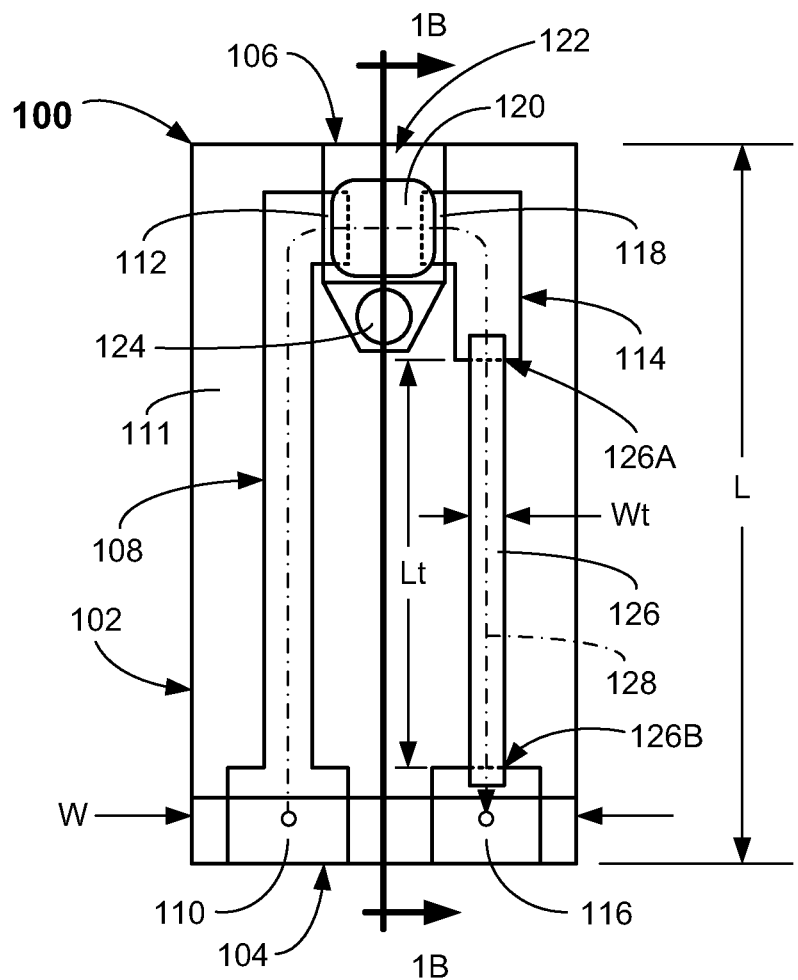
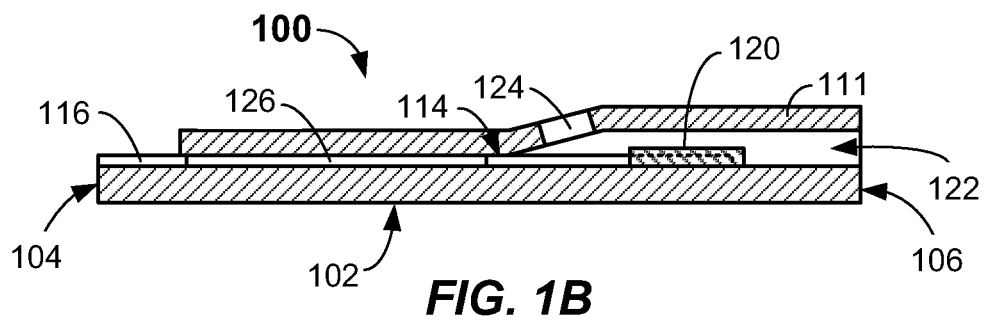
FIG. 1A
FIG. 1B

TEMPERATURE SENSING ANALYTE SENSORS, SYSTEMS, AND METHODS OF MANUFACTURING AND USING SAME

RELATED APPLICATIONS

The present application claims priority to U.S. Provisional Patent Application No. 61/413,365 filed Nov. 12, 2010, and entitled "TEMPERATURE SENSING ANALYTE SENSORS, SYSTEMS, AND METHODS OF MANUFACTURING AND USING SAME" which is hereby incorporated herein by reference in its entirety for all purposes.

FIELD OF THE INVENTION

The present invention relates to analyte sensors that may be used to detect an analyte concentration level in a bio-fluid sample, systems including the analyte sensors, and methods of using and manufacturing the analyte sensors.

BACKGROUND OF THE INVENTION

The monitoring of analyte concentration levels in a bio-fluid may be an important part of health diagnostics. For example, an electrochemical analyte sensor may be employed for monitoring of a patient's blood glucose level as part of diabetes treatment and care. An electrochemical analyte sensor may be employed, for instance, for detecting an analyte concentration level in a bio-fluid sample such as from a single sample of blood or other interstitial fluid. For example, the bio-fluid may be obtained from the patient using a lancet (e.g., by a pinprick or needle). Typically, after a bio-fluid sample has been obtained, the sample may then be transferred to a medium (e.g., to an analyte sensor) for measurement of the bio-fluid sample's analyte concentration level (e.g., a glucose analyte level).

It is established that such measurements may be somewhat affected by temperature, as the reagent and the electrochemical reaction may be temperature sensitive. Prior systems have included temperature sensing inside of an analyte testing meter (e.g., a temperature sensor inside of a blood glucose meter (BGM)). However, for various reasons, sensing of temperature inside of the meter, albeit achieving enhanced accuracy as compared to non-temperature compensated analyte meter systems, may induce some error when actual temperature on the sensor (at or near the reagent) is not properly compensated for. Accordingly, it may be beneficial to provide an analyte sensor adapted for bio-fluid analyte testing that may more closely or more elegantly account for temperature changes due to the actual temperature on the analyte sensor.

SUMMARY OF THE INVENTION

In a first aspect, the present invention provides an analyte sensor. The analyte sensor includes a first electrode having a contact engagement portion and a sensing portion; a second electrode having a contact engagement portion and a sensing portion; an active region provided in contact with, and extending between, the sensing portions of the first electrode and the second electrode; and a thermocouple portion comprising at least part of a conducting path from the active region to the contact engagement portion of the second electrode.

In yet another aspect, the present invention provides an analyte sensor. The analyte includes a base; a first conductor made of a first conductive material extending along the base, the first conductor having a first contact engagement portion and a first sensing portion; a second conductor extending along the base having a second contact engagement portion and a second sensing portion; an active region provided in contact with and extending between the first sensing portion and the second sensing portion; and a thermocouple portion connected between the second contact engagement portion and a second sensing portion of the second electrode, wherein the first contact engagement portion and second contact engagement are the only two contact engagement portions of the analyte sensor.

In another aspect, the present invention provides an analyte testing system. The analyte testing system includes an analyte sensor including a working electrode having a contact engagement portion and a sensing portion, a counter or reference electrode having a contact engagement portion and a sensing portion, an active region provided in contact with and extending between the sensing portions of working electrode and the counter or reference electrode, and a thermocouple portion connected between the contact engagement portion and a sensing portion of the counter or reference electrode and comprising at least part of a conducting path of the counter or reference electrode; and a temperature measurement circuit provided in electrical contact with the contact engagement portions.

In a method aspect, the present invention provides a method of testing an analyte sensor. The method includes providing an analyte sensor; coupling the analyte sensor to an analyte testing meter; measuring a temperature on the analyte sensor; burning a fuse member on the analyte sensor; and measuring an analyte value on the analyte testing meter.

In another method aspect, the present invention provides a method of manufacturing an analyte sensor. The method includes the steps of providing a base; forming a first electrode including a first material on the base; forming a second electrode on the base, the second electrode including a thermocouple portion of a second material different than the first material; applying an active region in contact with the first electrode and the second electrode, wherein the thermocouple portion is at least part of a conducting path from the active region.

Other features and aspects of the present invention will become more fully apparent from the following detailed description, the appended claims, and the accompanying drawings.

BRIEF DESCRIPTION OF THE DRAWINGS

FIG. 1A is a top plan view of an example embodiment of analyte sensor including a temperature sensing element provided according to a first aspect of the present invention.

FIG. 1B is a cross-sectioned side view of the example embodiment of analyte sensor of FIG. 1A taken along section line "1B-1B."

DETAILED DESCRIPTION

Figure 2A:
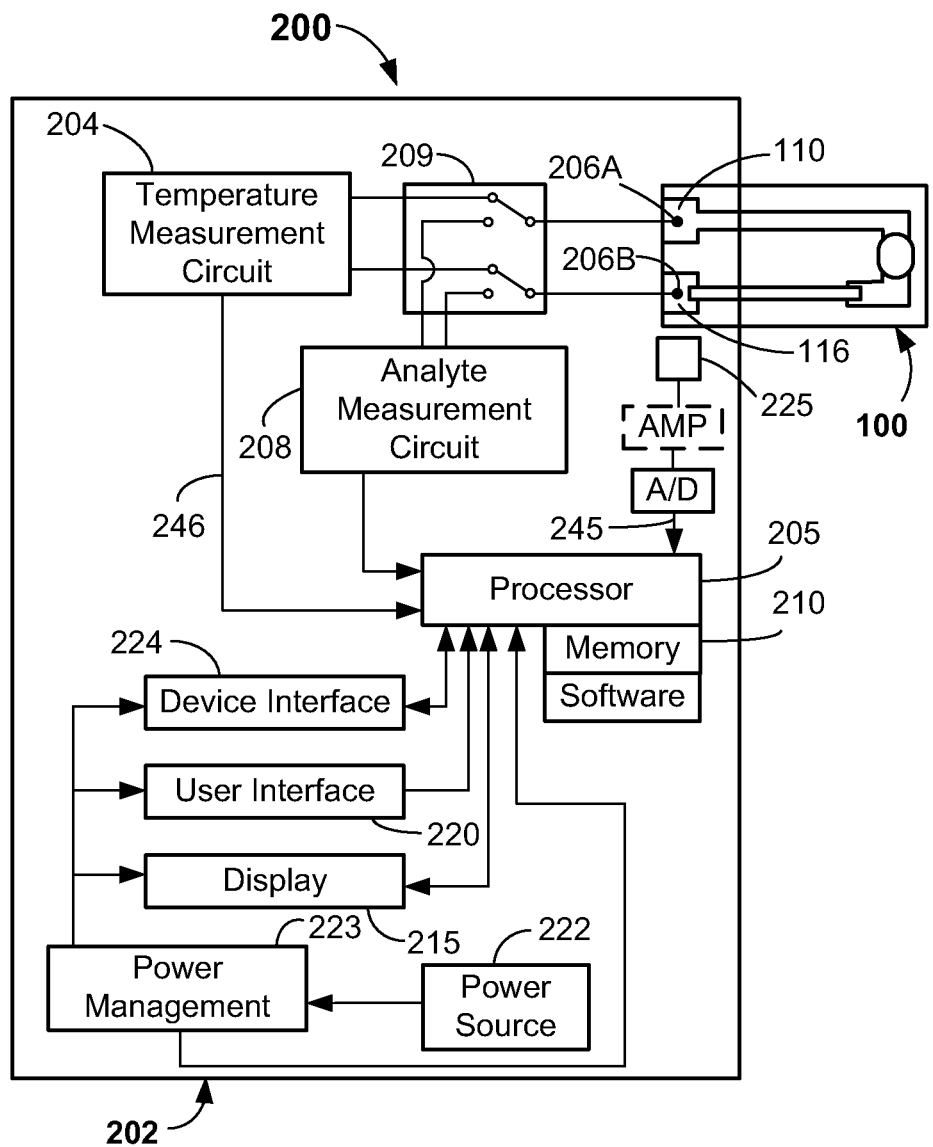
FIG. 2A is an example embodiment of an analyte testing system including on-body temperature measurement provided according to another aspect of the present invention.

According to some aspects of the present invention, an improved temperature-sensing analyte sensor is provided. As discussed above, although monitoring temperature inside the BGM may offer enhanced accuracy, it is desirable to sense the temperature at a location that is relatively closer to the actual site of the reaction, i.e., on the body of the analyte sensor (e.g., on the test strip). Including a temperature sensor on the body of the analyte sensor is referred to herein as having an "on-body temperature sensor."

For example, in analyte testing systems that are adapted to receive an analyte sensor in a port of an analyte testing meter, the part of the analyte sensor that actually contains the reagent may be located at a position outside of the physical confines of the analyte testing meter, and, therefore, may be exposed directly to the ambient environment. Because the thermal mass of the analyte sensor is substantially lower than of the analyte testing meter, the analyte sensor is prone to rapid changes in temperature and may equilibrate with ambient temperature very quickly. However, because the thermal mass of the analyte testing meter is relatively higher than the analyte sensor, the meter may more slowly equilibrate with ambient temperature. Accordingly, the temperature of the actual site where the reaction is taking place may be somewhat different than the temperature inside of the analyte testing meter. The present invention accounts for this difference.

In the way of a real-world example, a user may take the analyte testing meter (e.g., BGM) out of their pocket, and then may insert an analyte sensor into a port of the meter. The actual site where the reagent is located on the analyte sensor may be exposed to relatively cold weather (e.g., 30 degrees F. or less) and because of its relatively low thermal mass may quickly equilibrate so as to be at or very near to the ambient temperature whereas the temperature inside of the analyte testing meter may be relatively warmer.

In view of this concern, the present invention provides an analyte sensor having an on-body temperature sensor (e.g., that is resident on the body of the analyte sensor) such that the actual temperature of the reagent may be approximately accounted for. The analyte sensor may include first and second electrodes each having a contact engagement portion and a sensing portion, an active region provided in contact with, and extending between, the sensing portions of the first electrode and second electrode, and a thermocouple portion connected between the contact engagement portion and a sensing portion of the second electrode. The thermocouple portion may comprise at least a part of a conducting path from the active region to the contact engagement portion of the second electrode.

More simply, a thermocouple is embodied by the first and second electrodes thereby forming an on-body sensor. Accordingly, in some embodiments, the analyte sensor may include two, and only two, electrical contacts thereby significantly simplifying the act of making of an electrical connection with the analyte testing meter. The analyte sensor of the present invention may be used to measure any number of analytes, such as glucose, fructose, lactate, keytone, microalbumin, bilirubin, total cholesterol, uric acid, lipids, triglyceride, high density lipoprotein (HDL), low density lipoprotein (LDL), hemoglobin A1c, etc. The analytes may be detected in, for example, whole blood, blood serum, blood plasma, interstitial fluid, urine, etc. Other types of analytes may be measured provided a suitable reagent exists.

In other embodiments, an analyte testing system is provided. The analyte testing system includes an analyte sensor including a working electrode having a contact engagement portion and a sensing portion, a counter (or reference) electrode having a contact engagement portion and a sensing portion, an active region provided in contact with and extending between the sensing portions of working electrode and the counter (or reference) electrode, and a thermocouple portion connected between the contact engagement portion and a sensing portion of the counter (or reference) electrode and comprising at least a part of a conducting path of the counter electrode, and a temperature measurement circuit provided in electrical contact with the contact engagement portions (that may number two, and only two).

These and other embodiments of analyte sensors, analyte testing systems and apparatus including the analyte sensors, and methods of using and manufacturing the analyte sensor are described below with reference to FIGS. 1A-10.

FIGS. 1A-1B illustrate a top and a cross-sectioned side view, respectively, of a first example embodiment of an analyte sensor 100 provided according to a first aspect of the present invention. The analyte sensor 100 may include a sensor body including a base 102 preferably formed of an insulating material. The base 102 may have a first end 104 and a second end 106 opposite the first end 104 and spaced therefrom, and may be relatively planar in shape. The base 102 may be any suitable shape, such a rectangular, or other polygonal shapes. Other shapes may be used. The base 102 may be manufactured from of a suitable polymer material, such as a polycarbonate, polyethylene terephthalate (PET), polyethelyle naphthalate (PEN), polyimide, high density polyethylene, or polystyrene material, or combinations, for example. Other materials may be used. The base 102 may be manufactured by being stamped out of a sheet of material, thermally formed, extruded, or molded, for example.

The analyte sensor 100 includes a first electrode 108 (e.g., a working electrode) that in the depicted embodiment may extend along the base 102 from the first end 104 to the second end 106. The first electrode 108 includes a contact engagement portion 110 and a sensing portion 112. The contact engagement portion 110 may be enlarged relative to the extending portion of the electrode 108, located on the first end 104, and adapted to be contacted by an electrical contact of an analyte testing meter. A sensing portion 112 may be located on the second end 106.

Likewise, a second electrode 114 (e.g., a reference or counter electrode) may extend along the base 102 from the first end 104 to the second end 106. The second electrode 114 includes a contact engagement portion 116 and a sensing portion 118. The contact engagement portion 116 may be enlarged relative to an extending portion of the electrode, may be located on the first end 104, and may be adapted to be contacted by an electrical contact of an analyte testing meter. The contact engagement portions 110 and 116 may be made of the same material and have the same approximate shape and size. Like the sensing portion 112, the sensing portion 118 may be located on the second end 106. The sensing portion 118 may be positioned opposite of the sensing portion 112.

An active region 120, that may be located at on the second end 106, is provided in engaging contact with the first and second electrodes 108, 114. The active region 120 extends between the opposed sensing portions 112, 118. The active region 120 may be an electrochemically-active region including one or more catalytic agents or reagents adapted to react with a biological fluid that is provided in contact with the active region 120 during analyte measurement.

The first electrode 108 may be positioned partially underneath of the active region 120 such that there is an electrical coupling with the first electrode 108. The first contact engagement portion 110 is adapted to be in electrical contact with a first electrical contact of an analyte testing meter 202 (See FIGS. 2A-2B). The first electrode 108 and second electrodes 114 may be made from any suitable electrically-conductive material. Suitable conductive materials include carbon, graphite, noble metals such as gold, palladium, or platinum, silver, combinations of the aforementioned, or the like. In some embodiments, the electrodes may be made from a carbon/graphite PTF, silver/silver chloride, or an electrically-conductive ink such as a carbon- and silver-containing ink. As will be described more thoroughly below, the electrodes 108, 114 shall include sufficiently dissimilar materials to produce an on-body thermocouple sensor including a suitable electrical output according to an aspect of the invention.

Sensing portions 112, 118 of the electrodes 108, 114 may be formed on a surface of the base 102 and may include any suitable construction. For example, a single gap may be provided, or interleaved electrode fingers may form multiple gaps. The active region 120, as before described, may be applied over the sensing portions 112, 118. A suitable mask may be used for precise control and application of an applied area of the active region 120.

The active region 120 may be adapted to promote an electrochemical reaction between an analyte in the biological fluid sample and the catalytic agents or reagents included in the active region 120, or otherwise generate a detectable electrical current upon being exposed to the biological fluid sample. The mobile electrons produced may be conducted to an analyte testing meter 202 (FIGS. 2A-2B), for example. A voltage bias is generally applied to the electrodes 108, 114 of the analyte sensor 100 during the analyte measurement step of the testing sequence, i.e. when actually taking/recording a raw analyte concentration measurement.

One group of catalytic agents useful for providing the active region 120 may be the class of oxidase enzymes which includes, for example, glucose oxidase (which converts glucose), lactate oxidase (which converts lactate), and D-aspartate oxidase (which converts D-aspartate and D-glutamate).

In embodiments in which glucose is the analyte of interest, glucose dehydrogenase (GDH) may optionally be used. Pyrolloquinoline quinine (PQQ) or flavin adenine dinucleotide (FAD) dependent may also be used. A more detailed list of oxidase enzymes that may be employed in the present invention is provided in U.S. Pat. No. 4,721,677, entitled "Implantable Gas-containing Biosensor and Method for Measuring an Analyte such as Glucose" to Clark Jr. which is hereby incorporated by reference herein in its entirety. Catalytic enzymes other than oxidase enzymes may also be used.

The active region 120 may include one or more layers (not explicitly shown) in which the catalytic agents (e.g., enzymes) and/or other reagents may be immobilized or deposited. The one or more layers may comprise various polymers, for example, including silicone-based or organic polymers such as polyvinylpyrrolidone, polyvinylalcohol, polyethylene oxide, cellulosic polymers such as hydroxyethylcellulose or carboxymethyl cellulose, polyethylenes, polyurethanes, polypropylenes, polyterafluoroethylenes, block co-polymers, sol-gels, etc. A number of different techniques may be used to immobilize the enzymes in the one or more layers in the active region 120 including, but not limited to, coupling the enzymes to the lattice of a polymer matrix such as a sol gel, cross-linking the agents to a suitable matrix such as glutaraldehyde, electropolymerization, and formation of an array between the enzymes via covalent binding, or the like.

In some embodiments, a mediator may be included within the active region 120 to promote the conversion of the analyte to detectable reaction products. Mediators comprise substances that act as intermediaries between the catalytic agent and the electrode. For example, a mediator may promote electron transfer between the reaction center where catalytic breakdown of an analyte takes place and the electrode. Suitable mediators may include one or more of the following: metal complexes including ferrocene and its derivatives, ferrocyanide, phenothiazine derivatives, osmium complexes, quinines, phthalocyanines, organic dyes as well as other substances. In some embodiments, the mediators may be cross-linked along with catalytic agents directly to the first and second electrodes 108, 114.

In some embodiments, a lid 111 may be provided overtop of the base 102. The lid 111 may be fused or otherwise adhered to the base 102 by application of heat and pressure, for example. Other means of fastening the lid 111 may be employed, such as by the use of an adhesive or a sealant. The lid 111 may be formed, such as by stamping, cold forming, or heat forming. The lid 111 and base 102 when fastened together cooperate to form a cavity 122 that may extend from the second end 106 towards the location of the active region 120. The cavity 122 may provide a capillary channel into which a biological fluid sample applied at the end of the cavity 122 by a user may pass. The lid 111 may be manufactured from a deformable polymer material, such as polycarbonate, an embossable grade of polyethylenetherephthalate, or a glycol modified polyethylenetherephthalate, for example. Other types of materials may be used. A polyurethane dielectric material may be applied over an area encompassed by the lid 111 and may aid in sealing the lid 111 to the base 102. Further details of the structure of the lid 111 and base 102, as well as attachment details may be found in U.S. Pat. No. 5,759,364.

A vent 124 in the form of a hole or perforation may be provided at an end of the cavity 122 to improve capillary action and flow of the biological fluid sample into the cavity 122 from the second end 106 when applied thereat by the user. The cavity 122 may be at least partially formed and defined, for example, by the inner surfaces of the lid 111, base 102, and the upper surface of the active region 120. The cavity 122 may have any shape, but preferably a shape that promotes capillary action to cause a droplet of biological fluid to be drawn into the cavity 122 when applied to the entrance of the cavity 122 by the user. The bio-fluid sample may be drawn into the cavity 122 and come into intimate contact with the active region 120. The cavity 122 may have a length of about 2 mm to 5 mm, a width of about 0.5 mm to 1.5 mm, and a height of about 0.05 mm to 0.25 mm, for example. Other dimensions may be used.

In the depicted embodiment, the sensing portion 118 of the second electrode 114 includes a configuration making electrical contact with the active region 120. For example, the active region 120 may be provided/applied overtop of an end portion of the sensing portion 118 located opposite the sensing portion 112. The second electrode 114 may include a contact engaging portion 116 on the first end 104 that is adapted to make electrical contact with an electrical contact of an analyte testing meter (e.g. analyte testing meter 202 shown in FIGS. 2A-2B). In between the first end 104 and the second end 106 and extending between the sensing end 118 and the contact engaging portion 116 of the second electrode 114 is a thermocouple portion 126. In the depicted embodiment, the thermocouple portion 126 is connected between a cold sensing junction 126A on the sensing portion 118 and a hot sensing junction 126B on the contact engagement portion 116. The other portion of the thermocouple comprises a portion of the first electrode 108.

To establish a thermocouple, the thermocouple portion 126 may be manufactured from a material that is different than (dissimilar) to the material used to manufacture the first electrode 108. In the depicted embodiment, the thermocouple portion 126 comprises a part of the conducting path 128 (shown in phantom lines). The conducting path 128 during administration of a temperature test is the same as for an analyte measurement test. A voltage bias is applied across the contact engagement portions 110, 116 and a current is caused to flow through the first electrode 108, active region 120, and second electrode 114. In particular, the thermocouple portion 126 is part of the conducting path between the active region 120 and the contact engagement portion 116 of the second electrode 114. In other words, during the testing/measurement step of the testing sequence wherein a voltage bias is applied across the contact engagement portions 110, 116 and an analyte reading/measurement is obtained, the current for that reading/measurement passes through the thermocouple portion 126. Thus, it should be recognized that the thermocouple portion 126 lies in a direct current conducting path 128 during both the temperature measurement phase and the analyte measurement phase of the testing sequence. Generally, the temperature measurement phase takes place first, followed by the analyte measurement phase.

In the illustrated embodiment of FIGS. 1A-1B, the thermocouple portion 126 is a trace of a carbon-based material, such as a carbon-containing ink. In particular, in the depicted embodiment, the contact engagement portion 116 and the sensing portion 118 may be manufactured from the same material as the first electrode 108 (e.g., a gold film). The thermocouple portion 126 may then be applied overtop of the contact engagement portion 116 and the sensing portion 114 at the junctions 126A, 126B as a carbon-based trace.

In particular, the thermocouple portion 126 must comprise a different conductive material than a portion of the first electrode 108. In the depicted embodiment, the first electrode 108 may be a noble metal (e.g., a gold, platinum, or palladium film) and the thermocouple portion 126 may be a trace of a carbon-based material. However, any two sufficiently dissimilar materials may be used that provided a sufficient thermocouple effect.

By forming a thermocouple including the first electrode 108 and the thermocouple portion 126, a representative temperature measurement may be obtained by a temperature measurement circuit 204 (FIGS. 2A-2B) of the analyte testing meter 202 being electrically coupled thereto. The temperature measurement may be based upon thermoelectric principles (e.g., the Peltier-Seebeck effect). Once a temperature value has been obtained in the temperature measurement phase, that temperature value may be used to provide a temperature correction constant ($C_T$) to appropriately adjust the analyte measurement taken on the analyte sensor 100 for temperature on the analyte sensor 100 at or near the location of the active region 120. Accordingly, the actual ambient temperature on the analyte sensor 100 at a location near the site of the active region 120 may be approximately accounted for. This temperature correction may be in addition to a calculation adjustment that is made to accommodate for lot-to-lot or batch-to-batch variations wherein a calibration constant ($C_C$) is determined and used in the calculation of the analyte concentration.

In the depicted embodiment, the analyte sensor 100 may include two, and only two, contact engagement portions 110, 116. In other words, the contact engagement portions 110, 116 may be the only contact engagement portions on the analyte sensor 100. As mentioned above, this dramatically simplifies the making of an electrical contact with the analyte sensor 100, by requiring only two electrical contacts 206A, 206B in the analyte testing meter 202 that are adapted to engage the contact engagement portions 110, 116.

In some embodiments, the thermocouple portion 126 may be printed onto the base 102 and overtop of parts of the contact engagement portion 116 and the sensing portion 118 with a conductive ink by a screen printing process, ink jet process, or other deposition process, for example. The thermocouple portion 126 may have a width (Wt) of about 0.5 mm to about 1.5 mm, a length (Lt) of about 5 mm to about 25 mm, and a thickness of about 0.01 mm to about 0.1 mm, for example. Other sizes may be used. In a preferred embodiment, a conductive ink may be used, such as a carbon-based ink. However, any suitable conductive electrode ink may be used.

As shown in FIG. 1A, the analyte sensor 100 may include a length (L) of between about 15 mm and 35 mm, for example. The analyte sensor 100 may include a maximum width (W) of between about 3 mm and 10 mm, for example. Other length (L) and width (W) dimensions may be used.

In operation, upon insertion of a droplet of biological fluid sample into the cavity 122 such that the fluid comes into contact with the active region 120, and upon application of a suitable voltage bias across the electrodes 108, 114 (e.g., about 300 mV), an electrical current may be generated that may be proportional to a concentration of the analyte present in the biological fluid sample. This sensed electrical current may then be conducted by the electrical circuit including the first and second electrodes 108, 114, the thermocouple portion 126, the electrical contacts 206a, 206b, and an analyte measurement circuit 208 (See FIG. 2). The calculation of the analyte measurement may be by any currently known method. As discussed above, reagent variations are generally accounted for by using a calibration constant ($C_C$). However, either the calibration constant ($C_C$) or the analyte concentration calculation, according to an aspect of the invention, may be adjusted with a temperature compensation constant ($C_T$) that is obtained by the temperature measurement circuit 204 as will be described more fully below. The measured analyte concentration (appropriately compensated for analyte variations and temperature) may then be displayed in any suitable readout form, such as in a digital display of the analyte testing system 200 (e.g., a blood glucose meter) as shown in FIGS. 2A-2B.

Figure 2B:
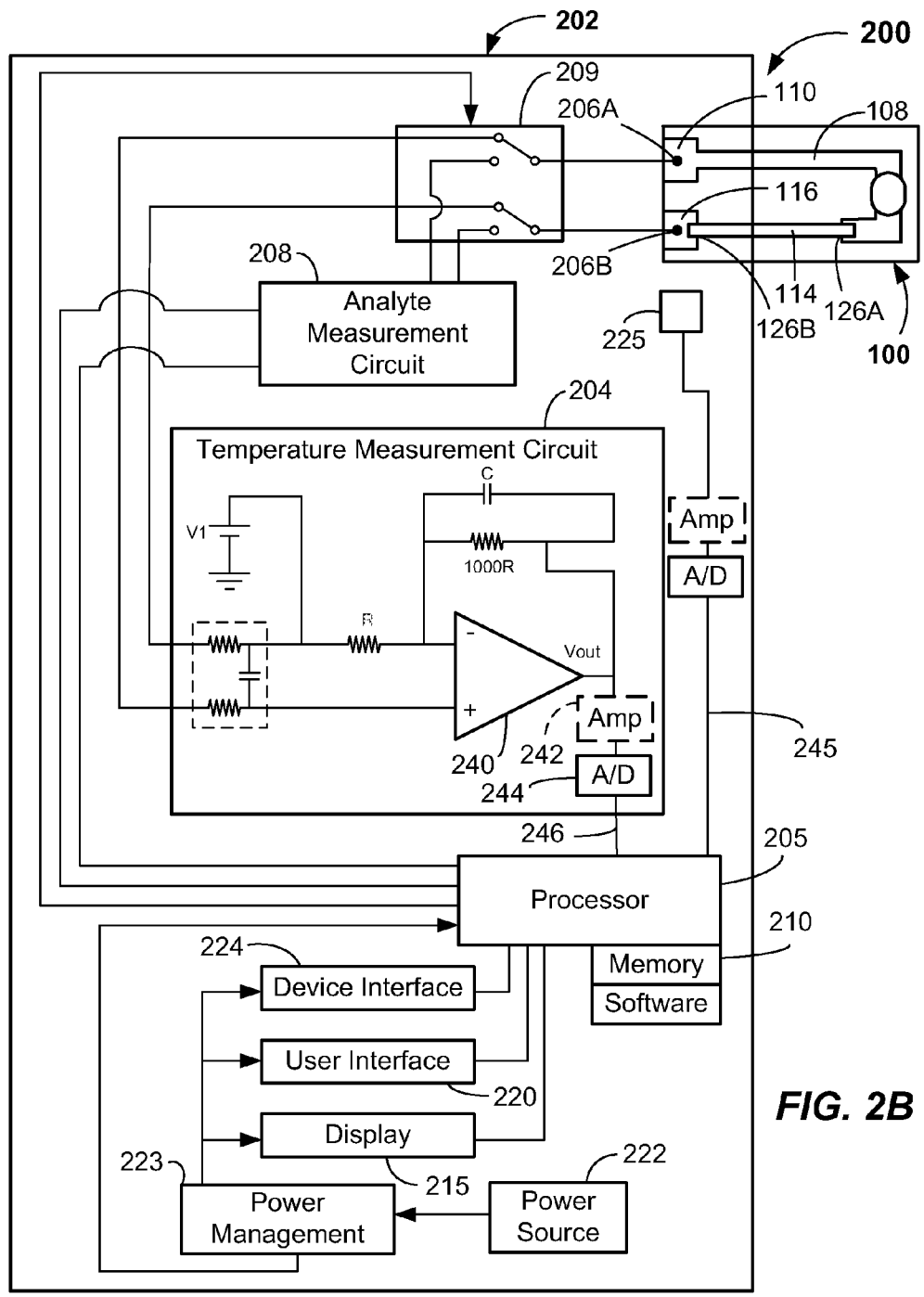
FIG. 2B is an example embodiment of an analyte testing system including a detailed view of the temperature measurement circuit provided according to another aspect of the present invention.

In more detail, FIGS. 2A-2B illustrate a analyte testing system 200 including an analyte testing meter 202 and an analyte sensor 100 of the type described in FIGS. 1A-1B electrically coupled thereto. In accordance with an aspect of the invention, the analyte testing meter 202 includes conventional components such as processor 205, memory 210, display 215 (e.g., a liquid-crystal display or the like), user interface 220 (e.g., push buttons, keys, a scroll wheel or ball, touch screens, or any combination thereof), power source 222 (e.g., a 3.0 V power source), power management 223, device interface 224, and electrical contacts 206A, 206B. The processor 205 may be any suitable processor. For example, the processor 205 may be any microprocessor device or collection of microprocessor devices that are capable of receiving the signals and executing any number of program routines, and may be a microcontroller, microprocessor, digital signal processor, or the like. For example, a suitable processor is a SoC microprocessor (e.g., a Cortex M3 equipped microprocessor) available from ST Microelectronics or Energy Micro. Data received and/or processed by the processor 205 may be stored in memory 210, which may store software routines that may be adapted to process raw analyte data and determine analyte measurement values, and carryout a temperature measurement sequence.

In operation, as an analyte sensor 100 including an on-board temperature sensor is inserted into a port of the analyte testing meter 202 and contact is made between the electrical contacts 206A, 206B and the contact engagement portions 110, 116 (thereby making contact with each electrodes 108, 114), the microprocessor 205 (e.g., a System On Chip (SOC)) may be awakened. This may be provided by a conventional resistance measuring circuit in the analyte measurement circuit 208, or by simply powering up the analyte testing meter 202, for example. A routine in software then causes a switch 209 to engage the temperature measurement circuit 204 to enable execution of a temperature measurement sequence. The switch 209 may be any suitable switch, such as a multiplexor.

The temperature measurement circuit 204, as best shown in FIGS. 2A and 2B, functions to record a changing voltage (Vout) that is proportional to a ΔT across the analyte sensor 100. In particular, the changing voltage (Vout) may be caused by a change in the temperature between the cold junction 126A and hot junction 126B of the analyte sensor 100 due to exposure to ambient temperature. The switch 209 may be activated by a suitable signal from processor 205 to cause an electrical connection between the temperature measurement circuit 204 and the analyte sensor 100. Once connected, the temperature measurement circuit 204 may execute a temperature sensing routine of the analyte testing sequence. Once started, a voltage differential may be provided to a differential amplifier 240 and an output may be provided that is proportional to the aforementioned ΔT. A Vout signal from the amplifier 240 may be amplified, if needed, by optional amplifier 242 and converted by A/D converter 244 to provide a digital output signal in line 246 to the processor 205 that is indicative of a ΔT between the cold and hot junctions 126A, 126B of the analyte sensor 100.

Likewise, the temperature sensing routine may cause an absolute temperature sensor 225 located in the port of the analyte testing meter 202 and proximate to the cold junction 126B to measure an absolute temperature as another voltage output. The absolute temperature digital signal received by the processor 205 in line 245 that is indicative of the temperature at the cold junction 126A and the voltage output digital signal representative of ΔT in line 246 may be summed by the temperature sensing routine operating in the processor 205 and may be stored in memory 210.

From these digital output values the temperature correction constant ($C_T$) may be obtained either directly or through the use of a look up table or via calculation using a mathematical function. This temperature correction constant $C_T$ may be used along with a calibration constant $C_C$ that is either manually input by the user, read from the packaging (e.g., in the case of multi-sensor packages), or otherwise obtained by interfacing with various electrical contact traces on the analyte sensor 100 (not shown).

Figure 3A:
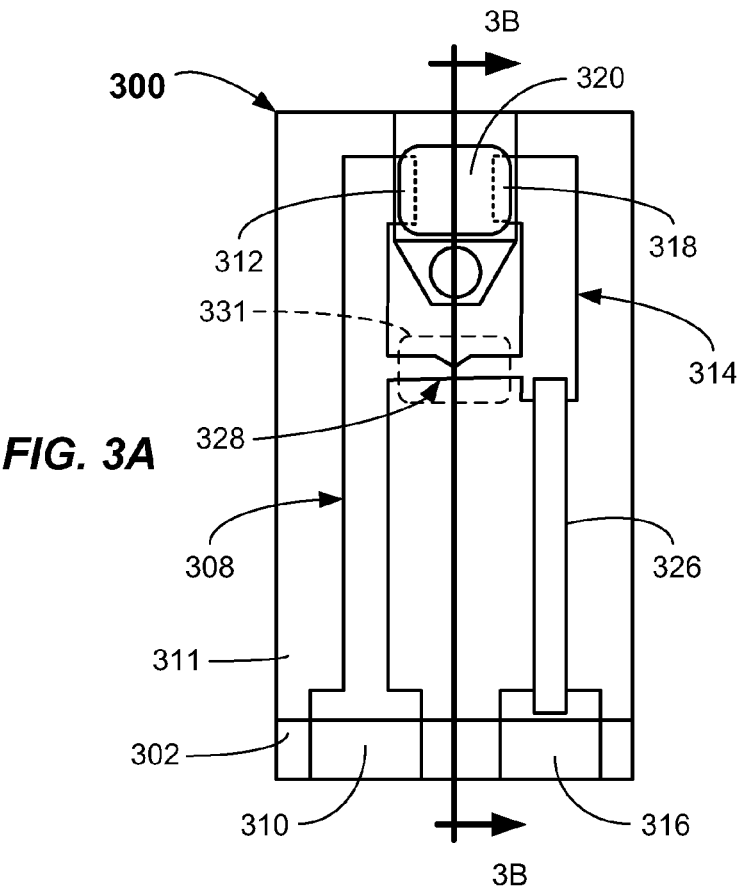
FIG. 3A is a top plan view of another example embodiment of an analyte sensor including a fuse member and on-body temperature sensor according to another aspect of the present invention.
Figure 3B:
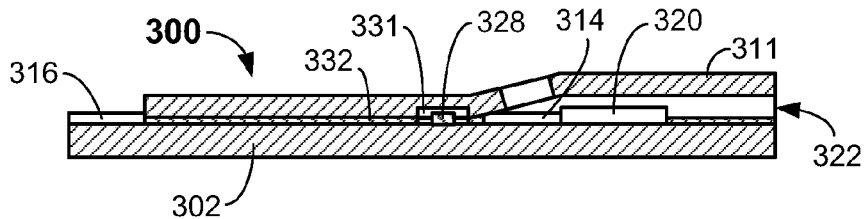
FIG. 3B is a cross-sectioned side view of the example embodiment of analyte sensor of FIG. 3A taken along section line "3B-3B."

FIGS. 3A-3B illustrate an example alternative embodiment of an analyte sensor 300 according to another aspect of the invention. The structure of the analyte sensor 300 is similar to the aforementioned FIGS. 1A-1B embodiment. In particular, the analyte sensor 300 includes a first electrode 308 having a contact engagement portion 310 and a sensing portion 312, a second electrode 314 having a contact engagement portion 316 and sensing portion 318, an active region 320 coupled to the electrodes 308, 314 at the sensing portions 312, 318, and a thermocouple portion 326 as above-described. However, in this embodiment, the analyte sensor 300 further includes a fuse member 328. The fuse member 328 may extend between, and electrically connect, the first electrode 308 and the second electrode 314. The fuse member 328 may be at least partially surrounded by a void 331. The void 331 may function to allow any gases from the burning of fuse member 328 a place to expand into.

Figure 4:
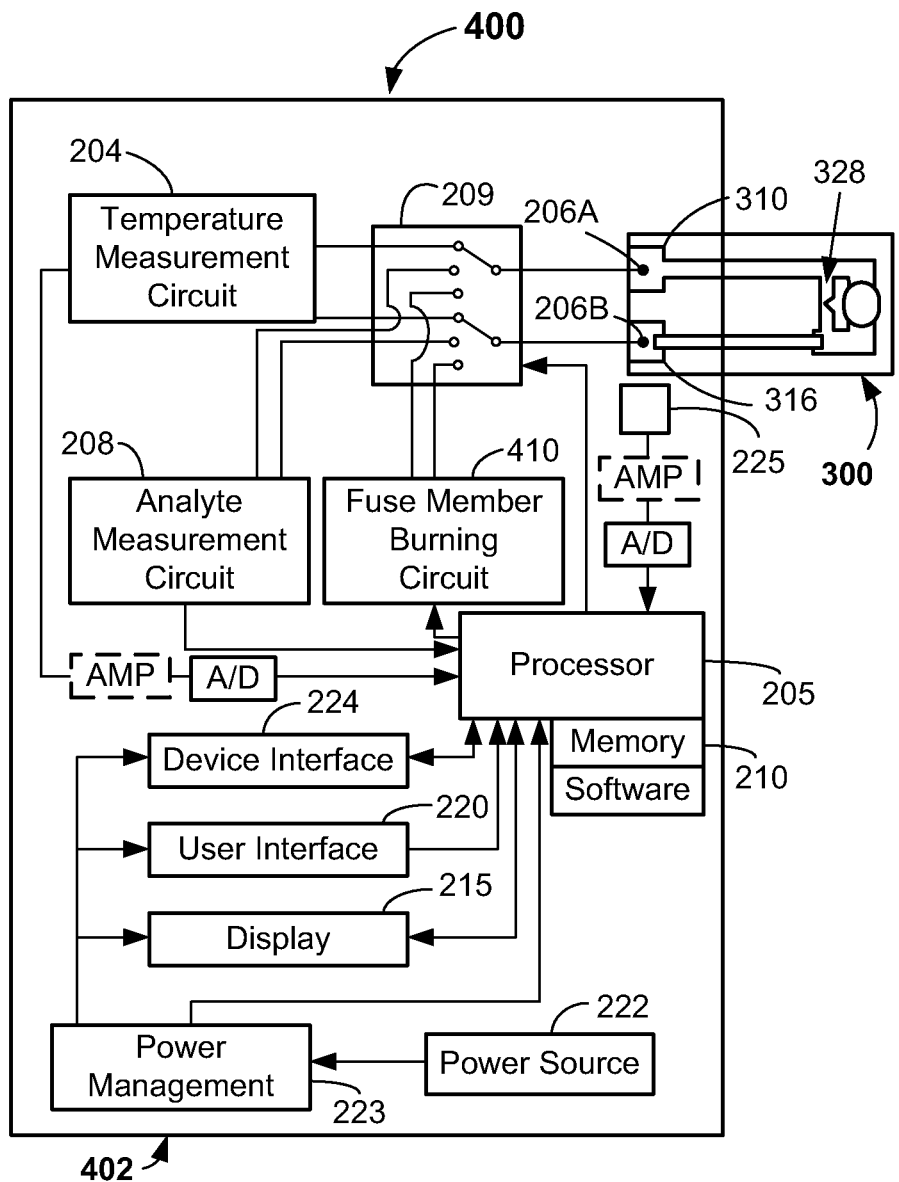
FIG. 4 is an example embodiment of an analyte testing system including on-body temperature sensing and fuse burning capability according to another aspect of the present invention.
Figure 5:
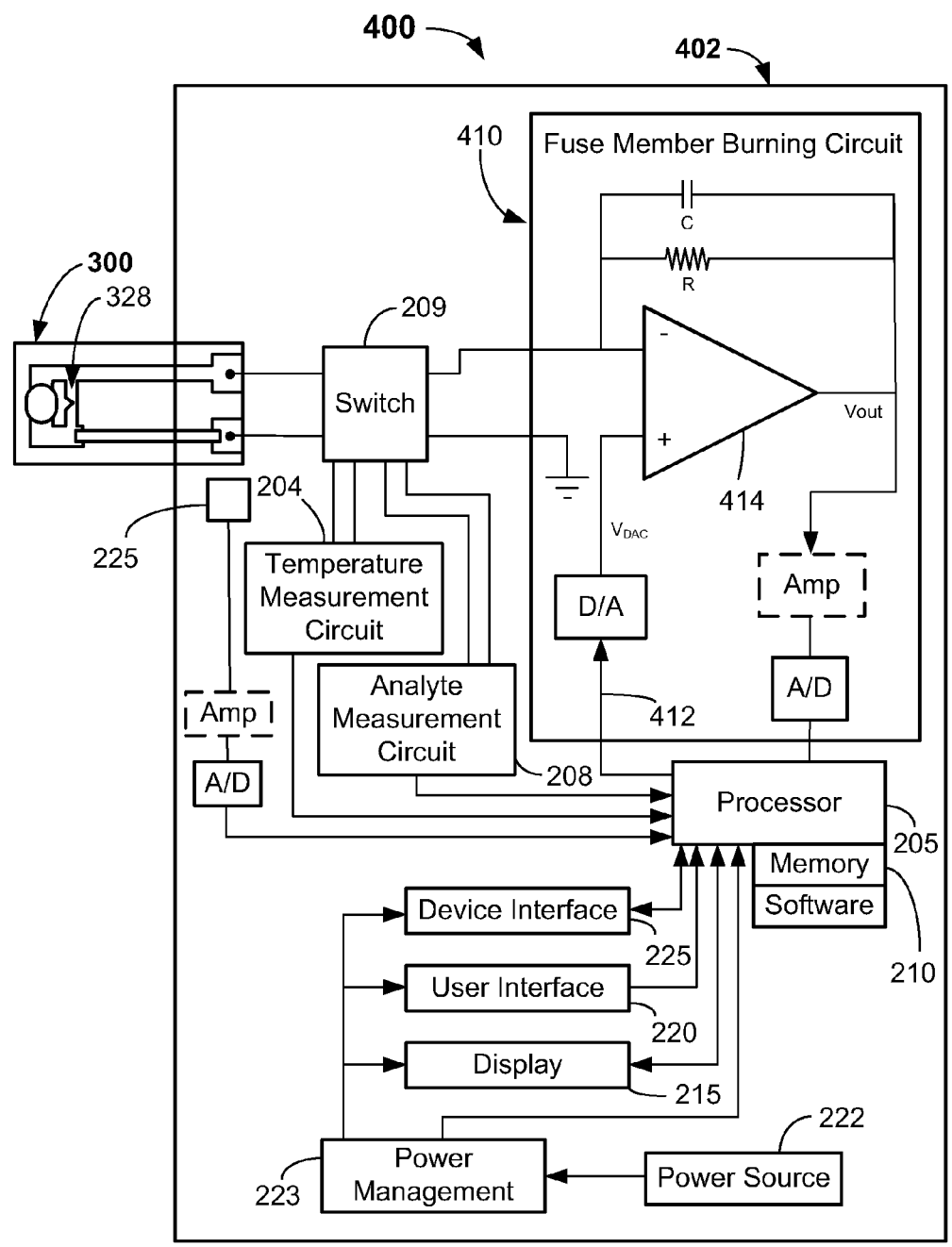
FIG. 5 is a detailed circuit diagram of an electrical circuit including a fuse member burning circuit adapted to burn a fuse member of an embodiment of analyte sensor according to another aspect of the present invention.

In more detail, the fuse member 328 may be formed of any suitable material that may be burnt (e.g., blown) by the application of a predefined voltage and/or current from a fuse member burning circuit 410 in an analyte testing meter 402 as shown in FIGS. 4-5. In the depicted embodiment, the fuse member 328 may be manufactured from the same materials as the first conductor 308 (e.g., a gold film). However, alternatively, the fuse member 328 may be manufactured from any suitable fusing material, and may be a different material than either the first or second electrodes 308, 314. In some embodiments, the fuse member 328 may include a fuse region of reduced area to control a burn location of the fuse member 328. The fuse region of reduced area may be formed by a notch or simply by reducing the thickness or other dimension of the fuse material in the fuse region as compared to other areas of the fuse member 328. Since the fuse member 328 is burned by utilizing the contact engagement portions 310, 316, the fuse member 328 should be configured to exhibit a burn value that is less than a voltage bias that will be applied to the analyte sensor 300, i.e., across the active region 320 during the analyte measurement phase of the analyte testing sequence. The burn value (Vb) is defined herein as a value of voltage or current that causes the fuse member 328 to burn fully (fail) thereby eliminating an electrical path across the fuse member 328, i.e., effectively burning (or blowing) the fuse member 328. Generally, the applied bias voltage across the analyte sensor 300 during an analyte measurement sequence is of the order of about 275 mV to about 625 mV. Therefore, in some embodiments, the burn value (Vb) for the fuse member 328 should be about 250 mV or less. In this way, the fuse member 328 may be included in a way that does not require additional electrical contacts on the analyte sensor 300. As shown, the fuse member 328 may be sandwiched between the base 302 and the lid 311. A sealant 332 may be used to secure the lid 311 to the base 302 should cause the fuse member 328 be sealed relative to the cavity 322. Optionally, the lid 311 may be compressed and thermally formed through application of heat and pressure to seal the lid 311 to the base 304 and seal around the void 331 and fuse member 328.

In the depicted embodiment, the fuse member 328 may be burnt/blown so that the analyte sensor 300 includes an easy mechanism to determine whether the analyte sensor 300 has been previously used. For example, functionality within a fuse member burning circuit 410 may burn the fuse member 328 as part of the testing sequence for each analyte sensor 300. Optionally, functionality within the temperature measurement circuit 204 or analyte measurement circuit 208 may carry out the burning of the fuse member 328.

Additionally, as part of the analyte testing sequence, functionality within the temperature measurement circuit 204, analyte measurement circuit 208, or fuse member burning circuit 410 as shown in FIGS. 4-5 may, before carrying out an analyte testing sequence, first carry out a check for a presence of a burnt fuse member 328. If detected, the functionality may reject the analyte sensor 300, issue a warning, or otherwise disallow any further testing on the analyte sensor 300. Detection of a burnt fuse member 328 may usually be indicative that the analyte sensor 300 may have been previously used.

To achieve a burn value (Vb) for the fuse member 328 of about 250 mV or less, the fuse region of reduced area of the fuse member 328 should be made to be relatively very small. For example, the cross-sectional area may be about $1.0 \times 10^{-5}$ $cm^2$ or less if a gold material is used to manufacture the fuse member 328. For a carbon-based material, the cross-sectional area may be about $3.7 \times 10^{-5}$ $cm^2$ or less. Thus, for a 10 mil wide carbon-based burn member, the thickness should be less than about 15 82 m.

Figure 3C:
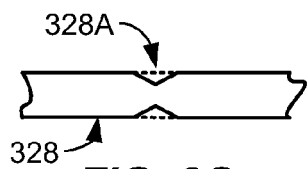
FIGS. 3C-3E are example embodiments of fuse members including reduced area fuse regions according to aspects of the present invention.
Figure 3D:
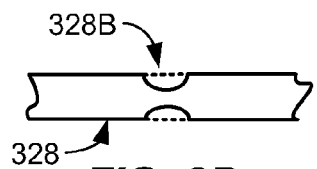
Figure 3E:
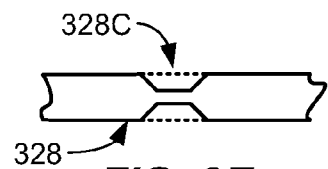

The precise dimensions of the fuse member 328 may be controlled by producing the fuse region to an oversized dimension in a first step, and then laser ablating some of the material away via the application of a suitable laser (e.g., an excimer, YAG, or $CO_2$ laser). In this way, as best shown in FIGS. 3C-3E, the dimensions of the fuse regions 328A, 328B, 328C of the fuse member 328 may be precisely formed and controlled, wherein the dotted lines represent the location of the oversized fuse region and the solid lines are the resultant configuration after the laser ablation has taken place.

Now referring to the analyte testing system 400 of FIGS. 4-5, the fuse member burning circuit 410 of the analyte testing meter 402 will be described in detail. The fuse member 328 of the analyte sensor 300 will be burned after the temperature measurements are obtained by the temperature measurement circuit 204 and sensor 225 and before the analyte measurement on the analyte sensor 300 is obtained by analyte measurement circuit 208. To undertake the burn sequence, a signal to the switch 209 from the processor 205 connects the fuse member burning circuit 410 to the analyte sensor 300. A signal in line 412 then ramps up the voltage ($V_{DAC}$) to the amplifier 414 to an appropriate level where the fuse member 326 is burned thereby creating an electrical open across the fuse member 328. This voltage is designed to be less than the voltage bias applied across the analyte sensor 300 during the next analyte measurement step of the sequence carried out by the analyte measurement circuit 208. Typically, the applied voltage bias will be about 300 mV during the analyte measurement phase of the sequence. Therefore, the voltage for the burn of fuse member 328 should be less than that; preferably less than about 250 mV, for example. Other lower voltages may be used, depending upon the burn value of the fuse member 328.

Vout may be monitored to determine the occurrence of the burn of the fuse member 328. For example, a slope checking algorithm may be used to test Vout for variations in slope of the Vout signal that are above a threshold value. Such slope excursions are indicative of fuse burning.

Once the burning of the fuse member 328 is accomplished, the switch 209 is again activated and the analyte measurement is undertaken by analyte measurement circuit 208. As is discussed below, the previously obtained temperature compensation constant ($C_T$) is used to adjust the raw measured analyte value (RMAV) to compensate for temperature at or near the location of the reagent on the analyte sensor 300.

Figure 6:
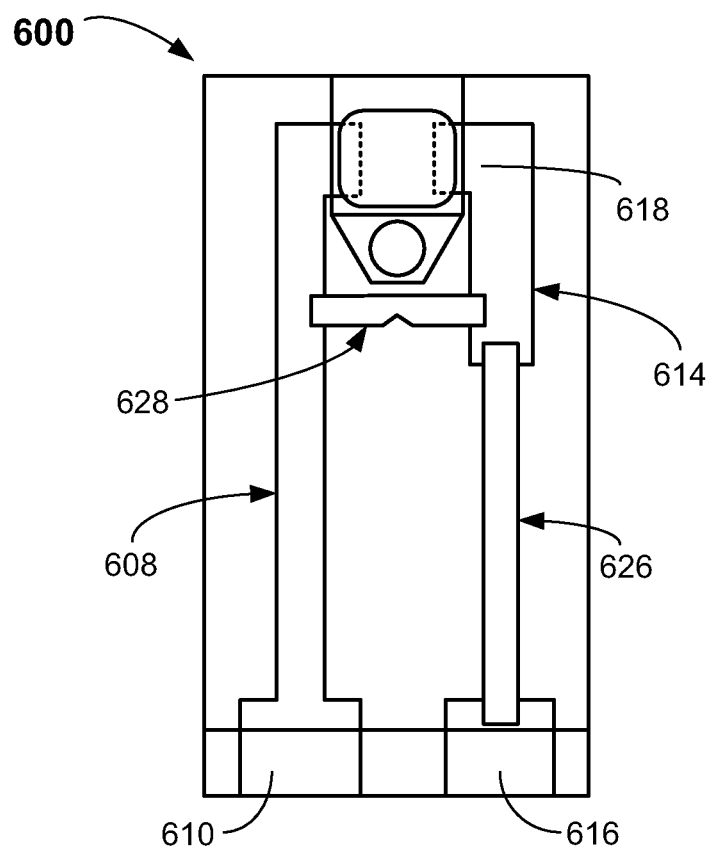
FIG. 6 is a top plan view of another example embodiment of an analyte sensor including an on-body temperature sensor and fuse member according to an aspect of the present invention.

FIG. 6 illustrates a variant of the embodiment of FIG. 3A-3B wherein the fuse member 628 of the analyte sensor 600 is provided as a carbon-based trace extending between the electrodes 608 and 614. All other features are the same as in the FIG. 3A-3B embodiment. In this way, the dimensions and the burn value of the fuse member 628 may be carefully controlled by ink-jet printing of the carbon-based trace by application of a suitable fusible carbon-based ink.

The first electrode 608 and contact engagement portions 610, 616 may be manufactured from a second material, e.g., a noble metal thin film. The thin film may be a gold or platinum film, for example having a thickness of about 100 nm or less. All other features are the same as in the FIG. 3A-3B embodiment. In this way, the analyte sensor 600 may be readily prepared through the use of a deposition process to deposit the noble metal portions of the first electrode 608, sensing portion 618, and the contact engagement portions 610, 616 followed by providing the carbon-based trace forming the thermocouple portion 626 and the fuse member 628 by an ink-jet process. Additionally, the burn value (Vb) of the fuse member 628 may be carefully controlled via the ink jet deposition process.

Figure 7:
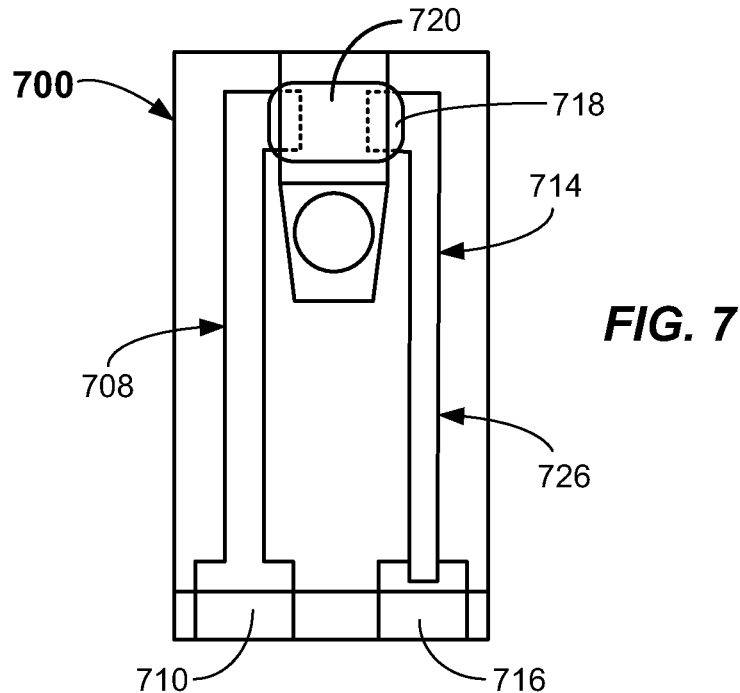
FIG. 7 is a top plan view another example embodiment of an analyte sensor including on-body temperature sensor according to an aspect of the present invention.
Figure 8:
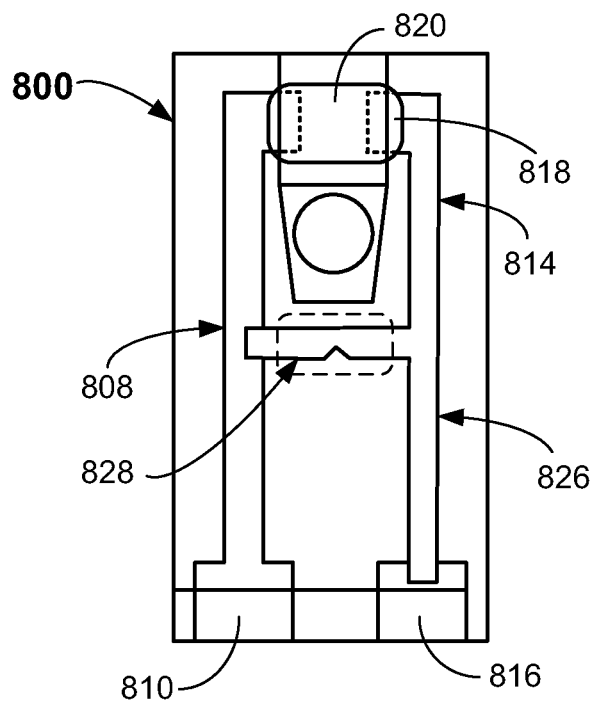
FIG. 8 is yet another example embodiment of an analyte sensor including an on-body temperature sensor and fuse member according to an aspect of the present invention.

FIG. 7 illustrates yet another variant of the embodiment of an analyte sensor 700 wherein the sensing portion 718 and the thermocouple portion 726 are each formed of a trace of carbon-based material. Optionally, as shown in FIG. 8, a fuse member 828 may be provided as a carbon-based trace extending between the electrodes 808 and 814 of the analyte sensor 800. In the depicted embodiment of FIG. 7, the first electrode 708 and contact engagement portions 710, 716 may be manufactured from a first material, e.g., a noble metal thin film. The thin film may be a gold or platinum film, having a thickness of about 100 nm or less, for example. All other features are the same as in the FIG. 1A-1B embodiment. In this way, the sensor 700 may be readily prepared through the use of a first deposition process to deposit the noble metal portions of the first electrode 708 and the contact engagement portions 710, 716 followed by providing the carbon-based trace forming the thermocouple portion 726 and the sensing portion 718 of the second electrode 714. The second electrode 714 and thermocouple portion may be formed via a suitable deposition process, such as by an ink-jet process depositing carbon-based ink. Active region 720 may be deposited thereafter.

As discussed above, FIG. 8 illustrates another embodiment of the analyte sensor 800. The sensor 800 includes a fuse member 828, thermocouple portion 826, and sensing portion 818, all being integrally formed from a carbon-based material. In this way, the sensor 800 may be readily prepared through the use of a first deposition process to deposit the noble metal portions of the first electrode 808 and the contact engagement portions 810, 816 followed by providing the carbon-based trace forming the thermocouple portion 826 and the sensing portion 818 of the second electrode 814. The second electrode 814 and thermocouple portion 826 may be integrally formed via a suitable deposition process, such as by an ink-jet process depositing carbon-based ink. Active region 820 may be deposited thereafter.

Figure 9:
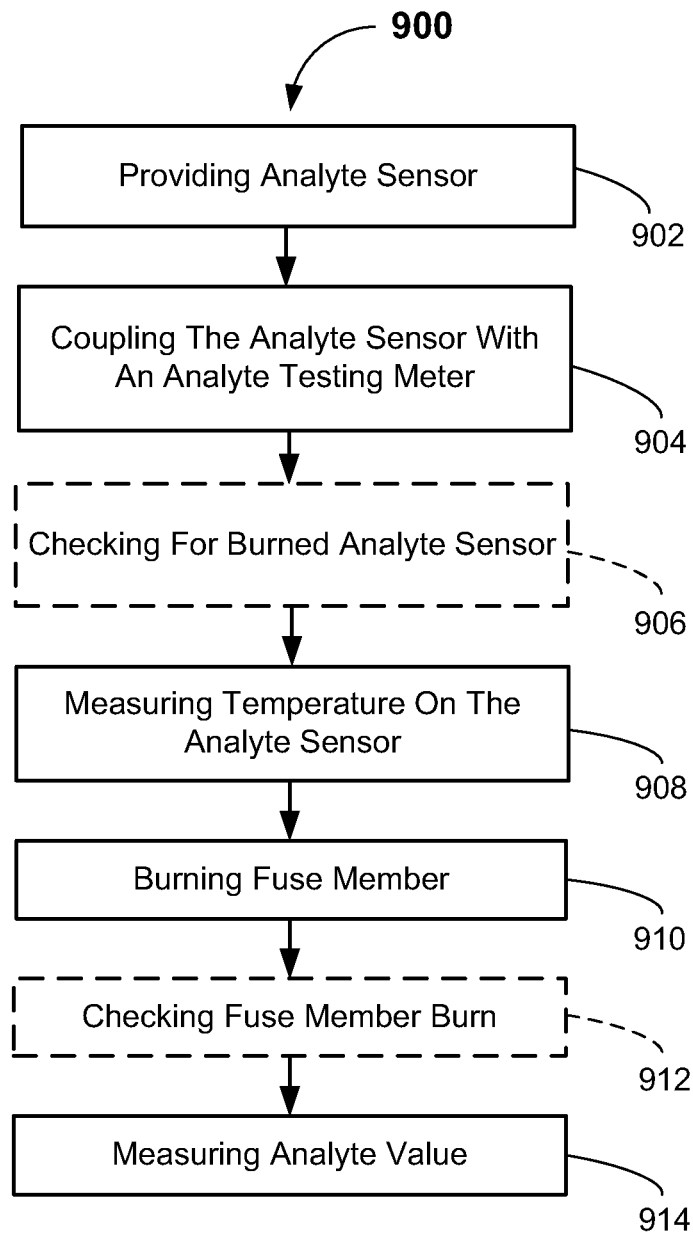
FIG. 9 is a flowchart illustrating methods of using the analyte sensor according to embodiments of the present invention.

Methods of testing embodiments of the analyte sensor 300, 600, 800 including a thermocouple portion 326, 626, 826 and a fuse member 328, 628, 828 according to an aspect of the invention will now be described with reference to FIG. 9. In one aspect, the method 900 includes the steps of providing an analyte sensor in 902, and coupling the analyte sensor to an analyte testing meter in 904 (e.g., via insertion in the meter 402 such that the contact engagement portions (e.g., 310, 316) of the analyte sensor (e.g., 300) make electrical contact with electrical contacts (e.g., 206A, 206B) in the analyte test meter (e.g., 402). Ambient temperature is measured by the use of a temperature sensor 225 (e.g., a thermister) positioned at a location in analyte testing meter 202 adjacent to the electrical contacts 206A, 206B. The temperature sensor 225 is used to measure the temperature at a point inside of the analyte testing meter 202 adjacent to the hot junction 126A. The actual temperature is the temperature as measured at the temperature sensor 225 plus (or minus) the temperature measured on the body of the analyte sensor 300 in 908 via the temperature measurement circuit 204. In particular, a ΔT is measured between the cold junction 326A and the hot junction 326B of the thermocouple portion 326. The difference between the cold and hot junction is added (or subtracted as the case may be) from the absolute temperature measurement obtained by the sensor 225 at or adjacent to the electrical contacts 206A, 206B. Accordingly, the actual temperature of the analyte sensor 300 at the cold junction 326B may be determined. This temperature, because it is very close to the active region 320, may be used to provide a suitable temperature compensation constant ($C_T$) for the analyte sensor 300. Circuit resistors and capacitors of the temperature measurement circuit are chosen to provide an appropriate temperature compensation constant $C_T$ based upon experimental testing.

Once the temperature of the analyte sensor 300 has been determined, a burning the fuse member 328 on the analyte sensor 300 may be accomplished in 910. The fuse member burning may be by the operation of a fuse member burning circuit (e.g., fuse member burning circuit 410 shown in FIGS. 4 and 5), for example. Finally, a measured analyte value is measured on the analyte testing meter in 914 via a conventional analyte measurement circuit 208. The calculation of the measured analyte value is achieved by entirely conventional calculation method and shall not be described further herein. The only variation is that an adjustment is made in the calculation for both temperature at the cold junction (using $C_T$) and for lot-to-lot or batch-to-batch calibration (Using $C_C$) as follows:

$$\text{Measured Analyte Value} = \text{RMAV} \times C_C \times C_T \quad \text{Equation 1:}$$

wherein
RMAV=Raw Measured Analyte Value,
$C_C$=Calibration Constant, and
$C_T$=Temperature compensation Constant.

The temperature compensation constant $C_T$ may be a linear factor, non-linear factor, or extracted from a lookup table based upon the output of the temperature measurement circuit 204, for example.

The method 900 may optionally include a step of checking to see if the fuse member (e.g., fuse member 328) of the analyte sensor (e.g., analyte sensor 300) is initially burned in 906 by testing, for example, a resistance across contact engagement portions 310, 316 of the analyte sensor 300 directly after coupling the analyte sensor 300 to an analyte testing meter 402 in 904. Once the fuse member 328 is actually burned in 910, the method 900 may optionally include a step of checking the fuse member burn in 912 wherein it is checked to see if the fuse member 328 of the analyte sensor 300 was properly burned. Again, the test for burn may be by testing a resistance across contact engagement portions 310, 316 of the analyte sensor 300. If resistance is not present, then it is determined that the fuse member 328 may be defective or a counterfeit, etc. and the analyte sensor 300 is determined to be not usable. In this condition, an error message may be provided to the user. Of course, if the fuse member 328 does not burn, then the analyte measurement in 1014 cannot be undertaken.

Figure 10:
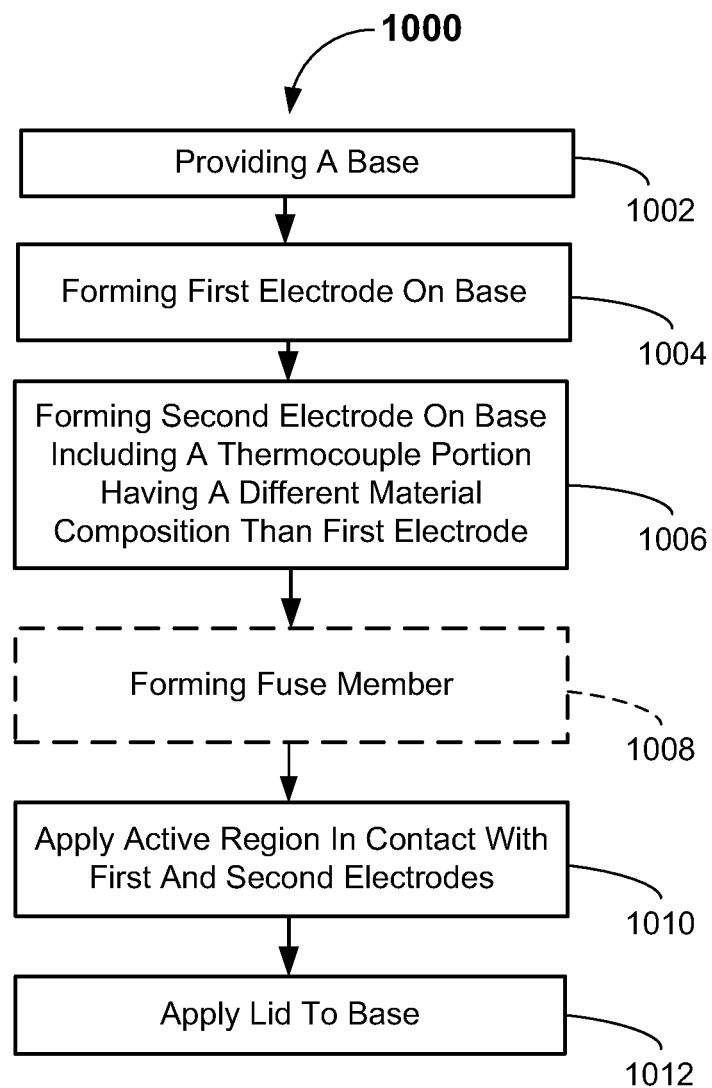
FIG. 10 is a flowchart illustrating methods of manufacturing the analyte sensor according to embodiments of the present invention.

Methods for manufacturing embodiments of the analyte sensors 100, 300 of the invention will now be described with reference to FIG. 10. The method 1000 includes the steps of providing a base (e.g., a base of insulating material) in 1002, and forming a first electrode on a surface of the base in 1004. The method 1000 also includes forming a second electrode on the base in 1006. The second electrode includes a thermocouple portion having a different material composition as compared to the material composition of the first electrode. In some embodiments, the thermocouple portion may constitute only a portion of the second electrode. For example, a first portion of the second electrode may include a sensing portion and a contact engagement portion, and the thermocouple portion may extend there between. The thermocouple portion may be deposited as a carbon-containing trace. An active region 120 may be applied to be in contact with at least a portion of the first electrode and at least a portion of the second electrode in 1010. In some embodiments, the active region 120 is provided in contact with only a small portion of the first and second electrodes. The electrodes may be formed to include a contact engagement portions adapted to be in electrical contact with first and second electrical contacts of an analyte testing meter (see FIGS. 2A-2B and FIGS. 4-5). According to the method 1000, a lid is applied overtop of the base in 1012 to form a cavity in the vicinity of the active region. As discussed above, in order to form a thermocouple, the first electrode and the thermocouple portion must be manufactured from different materials.

As discussed above, the electrodes may be made of any suitable electrically-conductive material, and may be formed by any suitable method. For example, one of the electrodes may be formed with a conductive ink (e.g., a carbon-based ink) using a screen printing, laser printing, or inkjet printing process, for example. Portions of the electrodes may be integrally formed, or formed as two separate components. In some embodiments, one electrode may be a metal material such as a noble metal (e.g., a gold film). The noble metal may be provided on the base by a sputtering deposition process. Optionally, the electrodes may be formed by adhering or forming a thin conductive film on the base.

The analyte sensors described herein may further include some form of underfill detection to determine whether a sufficient amount of the biological fluid sample is present in the cavity of the analyte sensor in order to carry out an acceptable analyte concentration measurement. For example, underfill detection may be provided by a method described in United States Application Publication 2009/0095071 to Wu et al. entitled "Underfill Detection System for a Biosensor." Described is a purely electrical solution wherein the method does not require the use of an additional electrode.

The foregoing description discloses only example embodiments of analyte sensors, systems and apparatus including the such analytes sensors, and methods of manufacturing and using the analyte sensors of the invention. Modifications of the above-disclosed analyte sensors, systems and apparatus incorporating them, and methods for manufacturing and using them, which fall within the scope of the invention, will be readily apparent to those of ordinary skill in the art.

Accordingly, while the present invention has been disclosed in connection with example embodiments thereof, it should be understood that other embodiments may fall within the spirit and scope of the invention, as defined by the following claims.

The invention claimed is:

1. An analyte sensor, comprising:
a first electrode having a contact engagement portion and a sensing portion;
a second electrode having a contact engagement portion and a sensing portion;
an active region provided in contact with, and extending between, the sensing portions of the first electrode and the second electrode; and
a thermocouple portion formed from the first and second electrodes and comprising at least part of a conducting path from the active region to the contact engagement portion of the second electrode.

2. The analyte sensor of claim 1, wherein the first electrode comprises a working electrode, and the second electrode comprises a counter or reference electrode.

3. The analyte sensor of claim 1, wherein the contact engagement portions are the only two contact engagement portions of the analyte sensor.

4. The analyte sensor of claim 1, comprising a base, the first electrode and the second electrode extending along the base.

5. The analyte sensor of claim 4, wherein the first electrode comprises a noble metal and the thermocouple portion comprises a carbon-based material.

6. The analyte sensor of claim 1, wherein the first electrode comprises a different conductive material than the thermocouple portion of the second electrode.

7. The analyte sensor of claim 1, wherein the thermocouple portion comprises a carbon-based material.

8. The analyte sensor of claim 1, comprising a fuse member extending between the first electrode and the second electrode.

9. The analyte sensor of claim 8, wherein the fuse member is manufactured from the same material as the first electrode.

10. The analyte sensor of claim 8, wherein the fuse member has a burn value that is less than about 250 mV.

11. The analyte sensor of claim 8, wherein the fuse member has a burn value that is less than a constant voltage bias adapted to be received across the active region during an analyte measurement test.

12. The analyte sensor of claim 8, wherein the thermocouple portion comprises a carbon trace extending from a reference junction at the contact engagement portion of the second electrode and a sensing junction adjacent to the fuse member.

13. An analyte sensor, comprising:
a base;
a first conductor made of a first conductive material extending along the base, the first conductor having a first contact engagement portion and a first sensing portion;
a second conductor extending along the base having a second contact engagement portion and a second sensing portion;
an active region provided in contact with and extending between the first sensing portion and the second sensing portion; and
a thermocouple portion formed from the first and second conductors and being connected between the second contact engagement portion and a second sensing portion of the second conductor;
wherein the first contact engagement portion and the second contact engagement portion are the only two contact engagement portions of the analyte sensor.

14. An analyte testing system, comprising:
an analyte sensor including:
a working electrode having a contact engagement portion and a sensing portion,
a counter or reference electrode having a contact engagement portion and a sensing portion,
an active region provided in contact with and extending between the sensing portions of working electrode and the counter or reference electrode, and
a thermocouple portion formed from the working electrode and the counter or reference electrode and being connected between the contact engagement portion and a sensing portion of the counter or reference electrode and comprising at least part of a conducting path of the counter or reference electrode; and
a temperature measurement circuit provided in electrical contact with the contact engagement portions.

15. The analyte testing system of claim 14, comprising an analyte measurement circuit provided in electrical contact with the contact engagement portions.

16. The analyte testing system of claim 14, comprising a fuse member blowing circuit provided in electrical contact with the contact engagement portions.

17. A method of testing an analyte sensor, comprising the steps of:
providing an analyte sensor;
coupling the analyte sensor to an analyte testing meter;
measuring a temperature on the analyte sensor;
burning a fuse member on the analyte sensor; and
measuring an analyte value on the analyte testing meter.

18. The method of claim 17 further comprising, after coupling the analyte sensor to an analyte meter, testing a resistance across contact engagement portions of the analyte sensor.

19. The method of claim 17 further comprising checking to see if the fuse member is burned.

20. A method of manufacturing an analyte sensor, comprising the steps of:
providing a base;
forming a first electrode including a first material on the base;
forming a second electrode on the base, the second electrode including a thermocouple portion of a second material different than the first material; and
applying an active region in contact with the first electrode and the second electrode
wherein the thermocouple portion is formed from the first and second electrodes and is at least part of a conducting path from the active region.

UNITED STATES PATENT AND TRADEMARK OFFICE
CERTIFICATE OF CORRECTION

PATENT NO. : 9,188,556 B2  
APPLICATION NO. : 13/884694  
DATED : November 17, 2015  
INVENTOR(S) : Hoi-Cheong Steve Sun et al.

Page 1 of 1

It is certified that error appears in the above-identified patent and that said Letters Patent is hereby corrected as shown below:

IN THE SPECIFICATION

In Column 4, Line 57, delete "polyethelyle" and insert -- polyethylene --, therefor.

In Column 6, Line 3, delete "Pyrolloquinoline quinine" and insert -- Pyrroloquinoline quinine --, therefor.

In Column 7, Line 61, delete "sensing portion 114" and insert -- sensing portion 118 --, therefor.

In Column 11, Line 34, delete "15 82 m." and insert -- 15 µm. --, therefor.

In Column 11, Lines 56-57, delete "fuse member 326" and insert -- fuse member 328 --, therefor.

In Column 13, Line 18, delete "hot junction 126A." and insert -- hot junction 126B. --, therefor.

IN THE CLAIMS

In Column 16, Line 56, in Claim 20, delete "electrode" and insert -- electrode; --, therefor.

Signed and Sealed this  
Seventeenth Day of May, 2016

Michelle K. Lee  
*Director of the United States Patent and Trademark Office*